United States Patent [19]
Mollet et al.

[11] Patent Number: 5,639,644
[45] Date of Patent: Jun. 17, 1997

[54] PLASMID DERIVED FROM *LACTOBACILLUS ELBRUECKII* SP.

[75] Inventors: Beat Mollet, Mollie-Margot; David Pridmore, Lausanne, both of Switzerland

[73] Assignee: Nestec S.A., Switzerland

[21] Appl. No.: 297,294

[22] Filed: Aug. 26, 1994

[30] Foreign Application Priority Data

Aug. 26, 1993 [EP] European Pat. Off. .............. 93202513

[51] Int. Cl.$^6$ .................. C12N 5/00; C12N 1/21; C12N 15/74
[52] U.S. Cl. ........................... 435/172.3; 435/252.3; 435/252.33; 435/320.1
[58] Field of Search ..................... 435/320.1, 172.3, 435/252.3, 252.33, 252.9

[56] References Cited

U.S. PATENT DOCUMENTS 5,426,047  6/1995  Ito et al. ..................... 435/252.3

OTHER PUBLICATIONS

Chagnaud et al. Can. J. Microbiol., 38: 69–74 1992.

*Primary Examiner*—Nancy T. Vogel
*Attorney, Agent, or Firm*—Knobbe Martens Olson & Bear

[57] ABSTRACT

The present invention concerns a plasmid derived from *Lactobacillus delbrueckii* sp. comprising at least the restriction map of the FIG. 1 or portion(s) thereof; the recombinant vector comprising the said plasmid, at least one DNA sequence capable of replication into *E. coli* and/or *Lc. lactis* and at least one marker.

The present invention concerns also the microorganism transformed by the said plasmid and/or by the said recombinant vector.

10 Claims, 7 Drawing Sheets

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 8140 base pairs
        ( B ) TYPE: nucleic acid
        ( C ) STRANDEDNESS: double
        ( D ) TOPOLOGY: circular     ( i i ) MOLECULE TYPE: DNA (plasmid)

( i i i ) HYPOTHETICAL: NO

( i v ) ANTI-SENSE: NO

( v ) FRAGMENT TYPE:

( v i ) ORIGINAL SOURCE:
        ( A ) ORGANISM: Lactobacillus bulgaricus
        ( B ) STRAIN: N2

( v i i ) IMMEDIATE SOURCE:
        ( B ) CLONE: Plasmid pN42

( i x ) FEATURE:
        ( A ) NAME/KEY: Origin of replication.
        ( B ) LOCATION: 5694..5758.
        ( A ) NAME/KEY: ORF1.
        ( B ) LOCATION: 1344..169.
        ( A ) NAME/KEY: ORF2.
        ( B ) LOCATION: 5965..7806.
        ( A ) NAME/KEY: ORF3.
        ( B ) LOCATION: 4718..5668.
        ( A ) NAME/KEY: ORF4.
        ( B ) LOCATION: 3116..3637.
        ( A ) NAME/KEY: ORF5.
        ( B ) LOCATION: 1779..2360.

( x i ) SEQUENCE DESCRIPTION: SEQ ID NO:1:

```
CCTAGGCTTG  AAATTGACGC  ATAGGCGCAA  AGGGAGCGGG  CGACAGGGGG  TAAAGCACGA     60
TAAATTCGTT  TTTTACAGAC  GTTCAGTCCA  TGTTGTCATA  TTTGTACTCC  CGTTTTTAGG    120
GCTGTTTTAA  AAGTATTTTT  AGCGGCGATT  TGTTAATTAT  AGCCCCTATA  CAAACATCTT    180
TTGTAAAAAG  CCTTTTTTCT  GTTCTTTCAA  CAAATCTAAC  TTACGTTGAT  GAAGAGCGAT    240
AGTGTCATCT  AGCTGTTTTA  AAAATGAGCC  TATTTTTTTT  TGTTCTTCCT  GACTAGGTTT    300
ATAGATTTTA  AATGATGAAA  ATTTAGAAAT  CCAATGACGT  TCATGACTTT  GAGGTACATA    360
TTTTATATTC  TTCAATGTAT  TAAACATAAA  ATAGAAATTG  TCAGAATTAT  CATTCAAACT    420
AAGTAATTTC  ATTGCGGAGC  TCTTAATTTT  AAAAGGGAAA  TCTACATAAT  GAGAGTCAGT    480
TGTAAAATCA  TCAAATATAA  CAACTGGATT  TTCTACGGTA  GCATTTTAA   TCCCGCTAAT    540
TTCATCTGTA  TAGCCCAATA  AGAAACTCTT  GCCTGCTGTT  AAAACAGGGG  TATTAAAATT    600
GTCATCGTAC  TCTGTAGATT  TGACAATATA  TTTTGTTGGT  TGCTCATAGT  TAAATACCTC    660
CCCCAACTTA  CACTGCTCCC  ATTCGTCACT  AAATCCTTCA  AACCGAATAG  CTGGATACCC    720
GCTCTTATAA  GCGAACATTT  TCTGCAGTAA  AGCGCTTTTT  AAGCATTTAA  GTTGCTGTTT    780
CTTTTCCTCA  TGTAAAGTGA  TTGCAGTATC  CAATTCAGAG  AAGAAGTTAG  CAATTCTTTC    840
TTGTTCAGAC  GTAGTTGGAA  ACGCAACAGA  CTGATTTCCG  ACAATATCCG  AGTTCAAATT    900
AACCTGACTT  CCCGGCTGAC  CATATTTGTT  CCAATATGGT  TTGAACATAA  GAAGCCATTG    960
AAACATAAAT  TCCTTATTAA  ATGTTGGGTT  GAGAAATATT  AAGAATCCAT  CGTGAACTCC   1020
```

-continued

```
TGTGTTAACG TAATTGATCA CTGGACTACC CACAGTAGCA GCAATACTTA ACAATAAATG   1080
TGGTTCTGTG ATAACACGCG TTTTAGATTG ACCAGCTTTT GAAATGTGTT GCGATAAGTG   1140
ATGAATGCGT CCTTTTGTT  CAGTGACATC GGATATTCTT AGCCATCCAA CATTTGAATT   1200
ATCATCGAAC CATTTGGGGT TAGAAATAGG TCTTGGACTC GCTCCACGTA CGATTTCCGC   1260
TTTGTTTTTT AACTTACACT GCTCCCAAGG ATCAGCGAAA CCTTTAAATC TTAATTGCGG   1320
ATATTTAGCT TGTGTATCAT TCATTATTTT TCCTCCGGTT TAATGTCTAA GGCCATTTTA   1380
TCAAATTAAA AATCAGCAAA ACCTATTTTG TGTCTGGTGG AACCAACAAG CGGCTAGAAA   1440
ATATGCTGCC AAACACCCTA AGAACAAAA  TATTGATAAC GAGCATACTT GGCATTAAAC   1500
GCCGTATAAG CTCATTTAAG CCGTTTTAAG TGTTATATGC ATAATTATAT TAAAACTGCT   1560
TTAAAATCGC TTAGAAGCAA GAATAGGCAG CTGAGTGGC  TGAATTGGCG ATGACTGAAC   1620
TAAGGACTAG GCCAAGAAAC TTTTGCACAG TCAACAATTC CCCGGACTAA TTCGGACTTT   1680
TTCTTTCTGG TCAGGTCTCC TAATGGTCAG TAAGGTCAGC CGCTTCAGCG GTCAATCGTG   1740
TATAATAATA ATCAAGATTG ACAAGAGGAG GGCTGACAAT GGCAAATAGC GCTGGCATGC   1800
TGTCAGTAGG TCAAATAGCT AAAATGCTGA AGACCAACAG ACAGAACATT TACAACGTGC   1860
TTAAAGCTGA GCATATTAAA CCTGACGGCT TCAATGACAA GCACTATTCA CTTTACAGCC   1920
CGGAAACAAT TCAAGAGATC AAGGCCGCTC TGTCTAAGAA GGCAACGCTG AGAAGTAAGA   1980
AGGTAGTAGC AAAAGAGCAG GCTGAAGAGA TAGCTGACTT GAAGAATCAG CTGTCAGAAC   2040
AGCAGAGATT GACAACCTGG CTACAGTCTC AGCTGGTTCA ACTTCAAGTA GAGGCTGACA   2100
AGCTCAGGAG TCAGAACAGC CAGTTACAGC TAGACAATGC AAAGACTCAG CTCCTTATTG   2160
GCCAGGTTGA CCAGGAGAAG ACAACACTGA AGGCCGAGAA TGACCGACTG AGCGCTGAAA   2220
ATAACAAACT AGGACAATTA ACCGATAAGG TGCTGAAGGA CGCTCAGAGA GCAGAAGAGG   2280
ACGCTCAGAA GGCTAAAGCT GATCTAGATA AAGCCCAAGC CCGGCGGGCT GGCTTATGGT   2340
CTAGAATCAC CAGGAATTAT TAAGAGTGGT ATAGCCGTTA TCTGACTTTG TGAAATTCCT   2400
TATTGGCTCT GTCAGATCAA GCGATTTTAA ACCTATACGA GTTTGTGAAT CCTAGTTTAC   2460
GGAATTGGGC GATAAGGAAG CCCGTCATTG CAAGGATAGA AGGTTAGTTC CAATAAGACA   2520
CATTATGTAA AGTTGTAAGT GGTATACCTG TAATTGATTG ACAGGAACTA TACACGGGCT   2580
AGACACTTGC CAGCATTGAC TGTAGCGGCT TTACAATGAC ACTAGATCTA CACTATAATT   2640
ACAGCGGAAA GAGAAAGGCT GAGCGGTCTC CTAATGGACA ACTACAACTG CCAGCCCGG    2700
CAACTTTGAG AGCCGTTAAA GAGCTCTCTC AGCATGGTTA GAGTATAGAA AGAGTGCTGA   2760
ACATGGACTT TAAAAAGGG  CTGAAGGGCT TGCAAGATCA GCAGACCCGG CTTGAAGCTA   2820
AACAGGAAGT ACTGTTAGAC ATCATGGCTG AGTTCTGGCC TAAAGTAGCT AAAGAAGGCA   2880
ATGACGTTGC TGAAGCGGTC AAGGTAGAAG ACCTGGCTGA ATGGTTCGCT AAGAACAGCC   2940
GGAAAACTGT TATTTGCGTG TCAGCAAGAC AGAAGACGGC TATGACCTGG CTTTTGAACC   3000
ACAACAGCCT TCAAGAGAAT TGTTATGGTA CGATGATCTT TATTGGCGGC TGGGTAAAAC   3060
AGCTGACCAA CTCAAAACGT AAATCTAAGG TCAAGACGCT AGAGGAAATT ATCTAATGGC   3120
GGTTTACAAA GAATGGACTG ATTCAGATCA TTTAGAGTTA GTCAAAAATT GGAAATTACA   3180
CGGGCTGACT AACGTTGAGA TAGCTCAAAG AATAGGCATT GCTGAGAAGA CTTTGTACGT   3240
ATGGTTGAAG AAGTCTCCTA AGCTGAAGAA GGCCATTAGA GGCGGCAAGG ATATTGCCAG   3300
GGCTAGGGCT GAGAATGCAC TGTATGAGCT TGCTCTTAAT GGCGATAGGC AAGCCCTTTT   3360
CTTTTGGCTC AAAAACAACT ACAGAGAACG CTACTCAGAC AAGCCGTTAA GCCCGGCTGA   3420
```

```
AGCCGATTTG ATGAGTCAGA AGGCAAGGCT GGCCAAATTA CAGGCTGACC TGGCTGAGGC   3480
TCAGCTGAAG GCCATTAAGG AAGACCAGGG AGACCAAGCA ACGCAATTAA ACAACCTGTT   3540
AGACAGTCTG AAGGAAGCCG TGTTAGATGA GGGAATTAGC CCCGATAACA TCGTTCCTAC   3600
TGGCAACGGC TTAATTATCG ATGATATTCC TGACTCTTAG GTTTACACGA CATTGACAGT   3660
GTAAACACAA GATAGCGGAA AATCTTCTGA TTATTATATT TACAAGCACT GTATATTGTG   3720
CTATTCTAAG ATGTGCTAAA CGGATTTGGG GAATGCAACT AACTGCTGTA AGGTATCAAC   3780
TTTTTTTGTT GCGCTCTTTA ATTCTTTAGC AAAAAGCTAG ATATCAAAAA AGAGCGAGAC   3840
CGGGTATTGC TTCACGGGTT CGCTCTTATT TTTTATCTG GCTAGTTGCC TACTGGTACT    3900
ATGCTGACAC CCTAGCGGCA TGTTTGCGGT ATTGCACTAC AGCGGCAACA ATGGTAAAAA   3960
TAATAATAGG TAACAAAAAA GCCTTTAGTA CTGGCAATAC TAGAGGCGGG CTGTGTTTAG   4020
CTCTGGCAAA GCTTAACACG GTTAGAATTA TATTCCGTAC CACATATGAT ACGTTAAAC    4080
GTAACACTCT GTCAAGGAGA ACATATCACC TTAAGGGTAC ATATAGTAGT TTCTTCTAA    4140
CATTATGTTG TAAAAACATA ACATTTTGTA GACAAACACT ATACTTCTAT GACTCTAACC   4200
ATGTTTAAGA CAGGCCAGGC TAACACCTAT TGGCCTGTTT TTTGTTGCCA AAATTTCAAA   4260
AGAAAGGCGG TAACAGCCGT GATTAAACAA CAAAACATTG ATGTTAGAGC GGCTATTAAA   4320
GCTTCTGGTC TGAAGCAATA TGAGGTAGCT ACTTTGATGA ATGTTTCAGC TAGCTATCTC   4380
AGCCAGCTTT TACTTCAACC ATTGTCAGAA GGCCATAAGA AGCGCATTAT GGCGGCGATT   4440
AAACAAGGCG AGTCATTGAA GGGAGAACAA GAATAATGAT GAGCTTAGAA GAACGTGAGC   4500
AAGAAATTGA AAAGGTAGTA CGCATTGCTG AAGCTGACTT CAACAACGCT TGTCAATTGC   4560
ATGCTATCAA CAAGGAAGAT GTTATTAAGA ACCATGCTTA CAAGTATGCT GAAGTGCTGA   4620
GGCTTCAGGA ATTGCTGGCA TTGAACAAGA CCATTAGGGA CGGTCTGAAC GGCATTGAAA   4680
TGTCAGTAGA TCTCATTGAG TAGCGGGGAG ACCCGCCATG AACAACAGTG AAAAAAACTC   4740
TCTAATGGCT GAACCGTATA ACTCAGACCG CAACGCCATT GACAGACTCA GAATCAACCA   4800
GAAGGCCTTA CAGGCGGGCT CTGTCAAGCG TGAAGAGGGC TACAACTCAG AGGGCTTAGA   4860
AATGGTCTCC TACACGGCTT ATAAGAGCGG CATTCAGTAT GTCATTTCTT CAGAAGCTGA   4920
AGGCGGCAAA ATGGTTATTA ACGAGACCTT CAGCAAGGTT CAACATCTAC TAATTGCCAG   4980
CTGGTATAGC CAGCCAGACA GAGCCAGCAA TTTCAGAATA CAGCTGACCT TTAAAGAGAT   5040
CTCAGAGGCG CTAGGAGTCA GCAGAAGCCA GGCTACAGCG CTCAGAAAGC AGCTGAGAGA   5100
GCTAATTACA CAGCTAGTAC GTTGTACTTT TGTTAACAGC AATAAGACG GCATAGACGC    5160
TGTCAATCTC TTTGCAGCTG GCAACTACAG TAAAGGGAAG CTGACAATGT GGTTAACTCC   5220
TAACATGGCT GAGCGGCTTC TGTCAGAAGA ATCATCTACG GAATATTTTC CGTTATCTTT   5280
ACTGAAGCTG AAAGGGACAG CCTATTATTT AGCCTTAAAG GTCATGCACA ACGCAAACAT   5340
TAATGCACGC TGGCATGCTG ACAGAGTTGA CAGATTGGGC TTAGAAAACA CGCTGAAGGC   5400
CTTGCCTACA CTCCCCGACC CGGTAAAACT CTCTAAAGGC AACAGCAGAA GCCTATACCT   5460
AAAAATCTTA ACTCCCCTGG CTAAAGCTAT TGAAGAGCTT GAAGCCGTCA CTGGCATTGT   5520
CGTTAGACCT AGCCAGCCAC TAAAGGGAAT GAAGACGAAA GATCTGTCTA AAGTCACTTT   5580
GAATGTCATT GATTGGGGAC AGGTTGATAT AGCCGAATTG ACCAGAAATA AGAGAAAACG   5640
CTTGCGAAAA AATAATGTTC GTGAGGACTA AAACTATATT TGTCCTAATT CGTATGTAGG   5700
TAATTATGGT CGCAAATGTA GGTAATTATG GTCGCAAATG TAGGTAATTA TGGTCGCATT   5760
GTGAAATTTA GGCAAGTGCC TTGAGGCATT GAGCCAGTAA GGAGTAAGCG CATTTTTTTA   5820
```

```
AAAAGCTTCA CTTGCTAATA GTTTAATAGT ATTAAAAGCA ACGGCTCAGC TTGACGCTGG   5880
CCTTGCTTGA AAATTGAAAA AAGATGAAAC AGCCAGGGAG AGCAGAGGCT TCTACTGGCC   5940
TGTTTTTAGA AGAAGGTATC TAGCATGAAC AATAACTTAG TTAAACCAAC AGATTTAAAG   6000
GGCTTGGTCT CTTTACCGGA ATACATTGCC AGCGTGGTTA GCATGGACTC TAAAGGCTTC   6060
TTTAGCTGTC TCAATCCGAA CCACCCGGAC AATCACCCTA GCATGTGTTT AGACCCTAAC   6120
CACCCGCAAT ATGTTCATTG CTTCAGTTGC GGCGTGTCCT ATGATCTGTT TGATTGTTGG   6180
GCGCTGATTA ATGACGGCGT GACAGAGACC AAGAAGAATA GCGCTGGCAA GGAAAAGCCA   6240
GTCTATAACT TCAATGCTGT AGCTTCAGAG ATTGCTGACC ATTACGGCTA TGCTCTTATT   6300
GGCGACCCGG CAAATGATCT CTATTCGGTA GAACCACCCT TGCCAGAACC ACCAGCAGAA   6360
CCAGCTCAGA CCAGCACCAA TTTTAGAGAG CAATTAGAAG ATTGGCATGC TAACTTGAAT   6420
CAGACTGACT ATCTTCAGAA GCGGGGAATC ACTCAGACAA CAGCAGAGAT TTTCAATTTA   6480
GGCTACTCCC CGTTGACCAA CAGCATTATT ATCCCTTACG GTCAGGACGG CTATTACGTT   6540
CAGAGGGCGC TGAATCCAAT TGAGAAGCGT GACCGCTACC GCTTCCCTAT TGGCCAGGCT   6600
AGAGCCTACA ACATTGAAGC ATTGGCTAAA TGCAAGACGG TATTCATCGT TGAAGGCCAG   6660
TTTGACGCTC TGTCAATCAT GCAAGAATCC GATGTAGGAG CTGTAGCAAC TTCAACCAGC   6720
CAGACTCGGC TTATTGTCAA GGCCTTACAG AAGTTCAAAG AGCAAGACCC AACAATTAAC   6780
CCGACTATCA TTCTCAGCAT GGACAACGAC AGAGCAGGCC AGAAGGCGAA TAGAGCCCTT   6840
CAGAGGGACT TAGAAGCCCT GGGCTTTACT TGCTATGTCA ACCCGGTTAA CGGCGACTAC   6900
AAGGACGCTA ACGAGTTCCT GGTAAAGGAT AGAGAGGGCT TCAGACAGAA ACTTCAGCAC   6960
GTCATCAATC AGCCCGACAA TTGGCTTGAC AATTACTATG CTGACATCAA AAAACGCCAT   7020
GACTACCCGG ACAATATCCC TACTGGCTTC AAGAATTTAG ATGATGAGCT TGACGGCGGT   7080
CTTCAGCCTA AACTGTATGT TTAGGCGCT GTCAGTTCGC TAGGGAAAAC GACTTTGCC    7140
TTGAATATTG CTGACAACCT GGCTAAACAG GGAGACATG TTTTCTTCTT CAGCATGGAA   7200
TCTAGCAAGA GAGAAGTGAC GGACAAGCTT TTAAGCCGGG CTAGCTGTCT CTCTAACGGC   7260
CATAAATGGA CTCAGCTTCA AGTCAGCCGG GGAGAATGGT TGAACAATGC TGAGGACAAA   7320
GAAGAGTTTG ACGGCCTGTT TAAAGCCTTC AGCCGTTACC AGCACTTCTT ACATATCTAT   7380
GACAATAGAG TTAAGGCAAG TCAGGTAAAA GACCTGGTCA ATAGTTGGCT TGACAACCAC   7440
CCGGACGAGA AGAAGCCGCT TGTAGTCGTT GACTATCTTC AGATCTTGCA AGCTGAGCAG   7500
GACAATGTGA CAGATAAGGC GAAAGTGACG GACAGCGTGA GTGTTCTCTC AGAGCTGACT   7560
AAACAGGCTG AAGTCCCTGT TCTGGTCATC TCATCATTGA ACCGGCTTC CTACTGGCAA    7620
GACGTAAGTT TTGAATCCTT CAAGGAATCC GGGGAAATTG AGTACTCAGC AGACGTTATG   7680
TTAGGATTAG AGTTCGCTCA TCGTGAAGAA TACATTACAG TTAAGGGCAA CGGCCATGTT   7740
GAATTGAACA AAGAGAAGTT TGACCAGCGG AAACAGGAAG TCCTAGACGG GTTGAAATGG   7800
TCATTCTGAA GAATCGAACT GGCAAGACAG GCGGTCATAT CTTCTTCAAG TACAACGCCA   7860
TGTTTAACAG CTACCAGGCA TGCACTGAGC AAGAGGCGGC AATACCCAAT AACTTTAATA   7920
AGTTGTTTCA TAGCAAGGAA GTAGGCAAGC CAATTGAAGC GGCTGTGCGT GATTACACGG   7980
TAGACCCGGT AACAGGCCTG GCAACAGAGA AGAAGCCCGA TAAATAGAAC TGAAGAAGCT   8040
GGCCAGGAAT GGCTGGCTTT TGTTTTGCCT TCAGACGCTC TCAGAAGCTC ATAGAGCCCC   8100
TCTGAGCCTG CATTGGTAGA TTTTTCCGGC CGAACACCCC                        8140
```

(2) INFORMATION FOR SEQ ID NO:2:

(i) SEQUENCE CHARACTERISTICS:
        (A) LENGTH: 1102 base pairs
        (B) TYPE: nucleic acid
        (C) STRANDEDNESS: double
        (D) TOPOLOGY: linear     (ii) MOLECULE TYPE: DNA (synthetic)

(iii) HYPOTHETICAL: NO

(iv) ANTI-SENSE: NO

(v) FRAGMENT TYPE:

(vi) ORIGINAL SOURCE:

(ix) FEATURE:
        (A) NAME/KEY: Other
        (B) LOCATION: 1...239
        (D) OTHER INFORMATION: lacS promoter of Lactobacillus
                bulgaricus
        (A) NAME/KEY: Other
        (B) LOCATION: 240...890
        (D) OTHER INFORMATION: Chloramphenicol acetyltransferase
                peptide of S. aureus
        (A) NAME/KEY: Other
        (B) LOCATION: 903...1102
        (D) OTHER INFORMATION: stem-loop terminator following
                galT gene of Lactobacillus lactis     (xi) SEQUENCE DESCRIPTION: SEQ ID NO:2:

```
GAATTCACCA ACGCTTTCAT TCACGCCTC  CCGAAGTACA TGCAAGAGGC TATATCGCCA     60
TCATTAGCAG CTTAATTGAA TATTTACTGG CTAAACTATT GAGTTTTCAA GGCTTCATAG    120
TTCTTTTTGG TGTGGAAGTT TAAATTACTA AAATATTTT  AGTAAAACAT CTTGGTTTAT    180
TTAGTAAACA AGTCTATACT GTAATTATAA ACAAGTTAAC ACACCTAAAG GAGAATTTCA    240
TGAACTTTAA TAAAATTGAT TTAGACAATT GGAAGAGAAA AGAGATATTT AATCATTATT    300
TGAACCAACA AACGACTTTT AGTATAACCA CAGAAATTGA TATTAGTGTT TTATACCGAA    360
ACATAAAACA AGAAGGATAT AAATTTTACC CTGCATTTAT TTCTTAGTG  ACAAGGGTGA    420
TAAACTCAAA TACAGCTTTT AGAACTGGTT ACAATAGCGA CGGAGAGTTA GGTTATTGGG    480
ATAAGTTAGA GCCACTTTAT ACAATTTTTG ATGGTGTATC TAAAACATTC TCTGGTATTT    540
GGACTCCTGT AAAGAATGAC TTCAAAGAGT TTATGATTT  ATACCTTTCT GATGTAGAGA    600
AATATAATGG TTCGGGGAAA TTGTTTCCCA AACACCTAT  ACCTGAAAAT GCTTTTCTC     660
TTTCTATTAT TCCATGGACT TCATTACTG  GGTTAACTT  AAATATCAAT AATAATAGTA    720
ATTACCTTCT ACCCATTATT ACAGCAGGAA AATTCATTAA TAAAGGTAAT TCAATATATT    780
TACCGCTATC TTTACAGGTA CATCATTCTG TTTGTGATGG TTATCATGCA GGATTGTTTA    840
TGAACTCTAT TCAGGAATTG TCAGATAGGC CTAATGACTG GCTTTTATAA TATGAGATAA    900
TCGAAAAAAA AAAGCTCAAA TTTTTGAGCT TTTTTTGTAT GTAATTGTCA TGCATGAAAA    960
TGTAATGGTA ATTGTGATAA TTATTAATAA AAAAATTGAT ATAATGAAGT GGATGAAAAA   1020
AAGACAGTTA AGAAGAAATA AAAATAAATT TAAAAGAGTA TCACTAGCTT TTTTTGGTTT   1080
AGTGATTATT TTAGCGGAGC TC                                            1102
```

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (i i) MOLECULE TYPE: DNA (synthetic)

(i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:3:

AGGAGGATCC TCTCATGAAC TTTAATAAAA TTG                33

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear     (i i) MOLECULE TYPE: DNA (synthetic)

(i i i) HYPOTHETICAL: NO

(i v) ANTI-SENSE: NO

(v) FRAGMENT TYPE:

(v i) ORIGINAL SOURCE:

(x i) SEQUENCE DESCRIPTION: SEQ ID NO:4:

TACAGTATCG ATTATCTCAT ATTATA                26

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear     (i i) MOLECULE TYPE: DNA (synthetic)

(i i i) HYPOTHETICAL: NO

(i v) ANTI-SENSE: NO

(v) FRAGMENT TYPE:

(v i) ORIGINAL SOURCE:

(x i) SEQUENCE DESCRIPTION: SEQ ID NO:5:

ATTGGAAGAA TTCACCAACG CTTTTCATTT C                31

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear     (i i) MOLECULE TYPE: DNA (synthetic)

(i i i) HYPOTHETICAL: NO

(i v) ANTI-SENSE: NO

(v) FRAGMENT TYPE:

(v i) ORIGINAL SOURCE:

(x i) SEQUENCE DESCRIPTION: SEQ ID NO:6:

GGTGGTGACG AAGACGATA 19

PLASMID DERIVED FROM *LACTOBACILLUS ELBRUECKII* SP.

FIELD OF THE INVENTION

The present invention concerns a new plasmid derived from *Lactobacillus delbrueckii* sp., a recombinant vector comprising said plasmid, the microorganism transformed by said plasmid and/or vector and the use of the plasmid and/or the vector for the transformation of microorganisms.

BACKGROUND OF THE INVENTION AND STATE OF THE ART

A successful biological transformation of an organism must satisfy the following three criteria:
1. Transforming DNA must enter the organism by physical or chemical means such as electrotransformation, treatment with inorganic ions, protoplast fusion, etc.
2. Transformants must be selected with the help of one or more markers from the non transformed cells in the population for instance by antibiotic resistance genes linked to the transforming DNA. This is best satisfied by either the isolation of a resistance gene against an antibiotic from the target host in question, or by the engineering of a known resistance gene with expression sequences (promoter and terminator) compatible with the target host.
3. Transforming DNA must be replicated (either autonomously or as part of the host genome). This is best satisfied by the isolation of replicating plasmids from the host to be transformed and to subsequently construct vectors able to replicate in a microorganism such as *Escherichia coli* (*E. coli*) or *Lactococcus lactis* (*Lc. lactis*) and in a specific target organism such as *Lactobacillus delbrueckii* subsp. bulgaricus (*L. bulgaricus*).

The international patent application WO92/14825 describes a plasmid pBULI having a length of about 7.9 kb and its derivative isolated from *Lactobacillus delbrueckii* subsp. bulgaricus M-878 strain.

The restriction map of this plasmid is characterized by the absence of restriction sites for BamHI, EcoRI, KpnI and PstI enzymes.

This plasmid is used as a vector for breeding various microorganisms such as lactic acid bacteria and the derivative of this plasmid is used as a shuttle vector (lactic acid bacterium—*Escherichia coli*).

Other shuttle vectors are described in the documents Canadian Journal of Microbiology (vol. 38 (1992) pp 69–74), ACTA MICROBIOLOGICA BULGARICA (vol. 27 (1991) 99 3–8) and in the Japanese Patent Application JP-A-4.218.381.

AIMS OF THE INVENTION

The present invention aims to provide a new plasmid derived from *Lactobacillus delbrueckii* sp. which can be used to transform specific microorganisms specially *Lactobacillus bulgaricus*.

Another aim of the invention is to obtain a recombinant vector comprising the said plasmid and which can replicate in *E. coli* and *Lc. lactis* and transform specific microorganisms, specially *Lactobacillus bulgaricus*.

DISCLOSURE OF THE INVENTION

Figure 1:
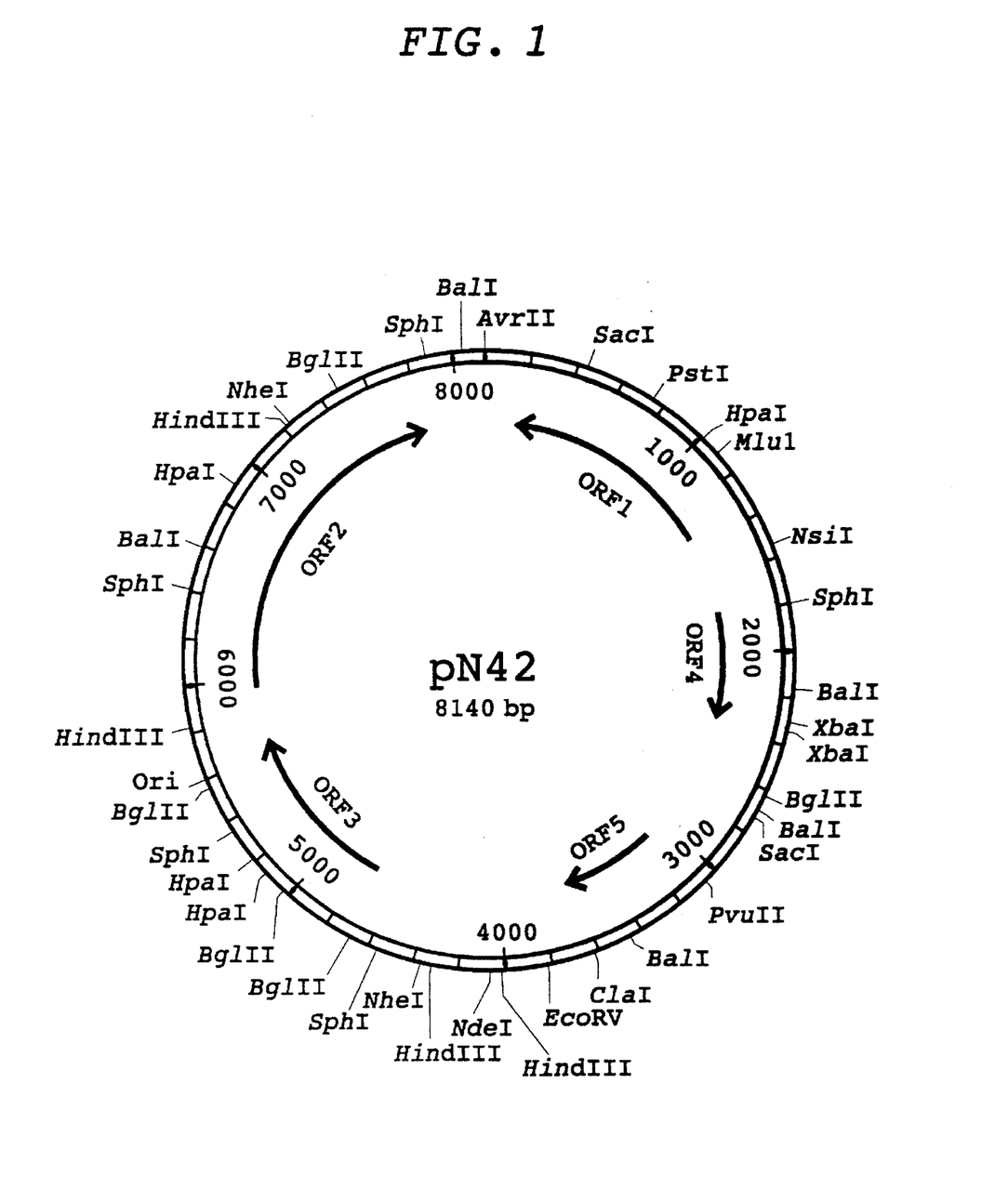

The present invention concerns a new plasmid derived from *Lactobacillus delbrueckii* sp. comprising at least the restriction map of the FIG. 1 or portion(s) thereof.

The plasmid according to the invention comprises at least the DNA sequence SEQ ID N° 1 and/or its complementary strand, or portion(s) thereof.

Furthermore, the present invention concerns a recombinant vector comprising the plasmid according to the invention, at least one DNA sequence capable of replication in *E. coli* and/or *Lc. lactis* and at least one marker.

The DNA sequence capable of replication in *E. coli* and/or *Lc. lactis* is constituted for instance by a specific plasmid, such as pDP193, which allows the recombinant vector to be freely cultured in either *E. coli* or *Lc. lactis* for molecular manipulations.

The marker comprised in the recombinant vector according to the invention, is a DNA fragment used as a reference for analytical purposes (i.e. a gene with known phenotype and mapped position) and/or a DNA fragment which is expressed in the microorganism transformed by the vector according to the invention.

This DNA fragment may be used also for the transformation of microorganisms in order to obtain for instance:
resistant strains to phages,
ropy strains (improved texturing properties),
probiotic strains,
strains producing new or improved enzymes (lipases, deshydrogenases, . . . ), aroma or flavor compounds, . .

The present invention concerns also the microorganism, preferably *Lactobacillus bulgaricus*, transformed by the plasmid and/or by the recombinant vector according to the invention.

Finally, the present invention concerns the use of the plasmid and/or the vector according to the invention for the transformation of microorganisms.

BRIEF DESCRIPTION OF THE DRAWINGS

The FIG. 1 represents the restriction map of the *Lactobacillus delbrueckii* sp. plasmid pN42 (Deposited in accordance with Budapest Treaty with the *Collection Nationale de Cultures de Microorganismes*, INSTITUT PASTEUR (CNCM), 25 Rue du Docteur Roux, 75724, Paris Cedex 15, France, under Registration No. 1-1682) according to the invention.

The FIG. 2 represents the construction of the plasmid pN42-Sub CB from the pJDC9 plasmid and pN42 plasmid.

The FIG. 3 represents the construction of pN42-Sub CE from the pJDC9 plasmid and pN42 plasmid.

The FIG. 4 represents the construction of pN42-Sub W and pN42-Sub X from the pUC19 plasmid and pN42 plasmid.

The FIG. 5 represents the construction of chloramphenicol transacetylase gene of pDP352.

The FIG. 6 represents the construction of the pDP193 plasmid.

The FIG. 7 represents the construction of pDP359 plasmid.

DESCRIPTION OF A PREFERRED EMBODIMENT OF THE INVENTION

The construction of pDP359, a *E. coli/Lc. lactis-L. delbrueckii* sp. shuttle vector according to the invention is characterized by the following features.

Firstly the incorporation of pDP193 allows the plasmid to be freely cultured in either *E. coli* or *Lc. lactis* for molecular manipulation, such as the addition of genes to be expressed in L. bulgaricus. Secondly the inclusion of a bona fide L. delbrueckii sp. plasmid in its entirety ensures that pDP359 contains all the sequences required for the replication of pN42 and hence must replicate in L. bulgaricus in the same fashion as pN42 in its host N42. Thirdly the inclusion of the chloramphenicol resistance gene engineered in pDP352 ensures a means to select for transformants in L. bulgaricus.

Figure 2:
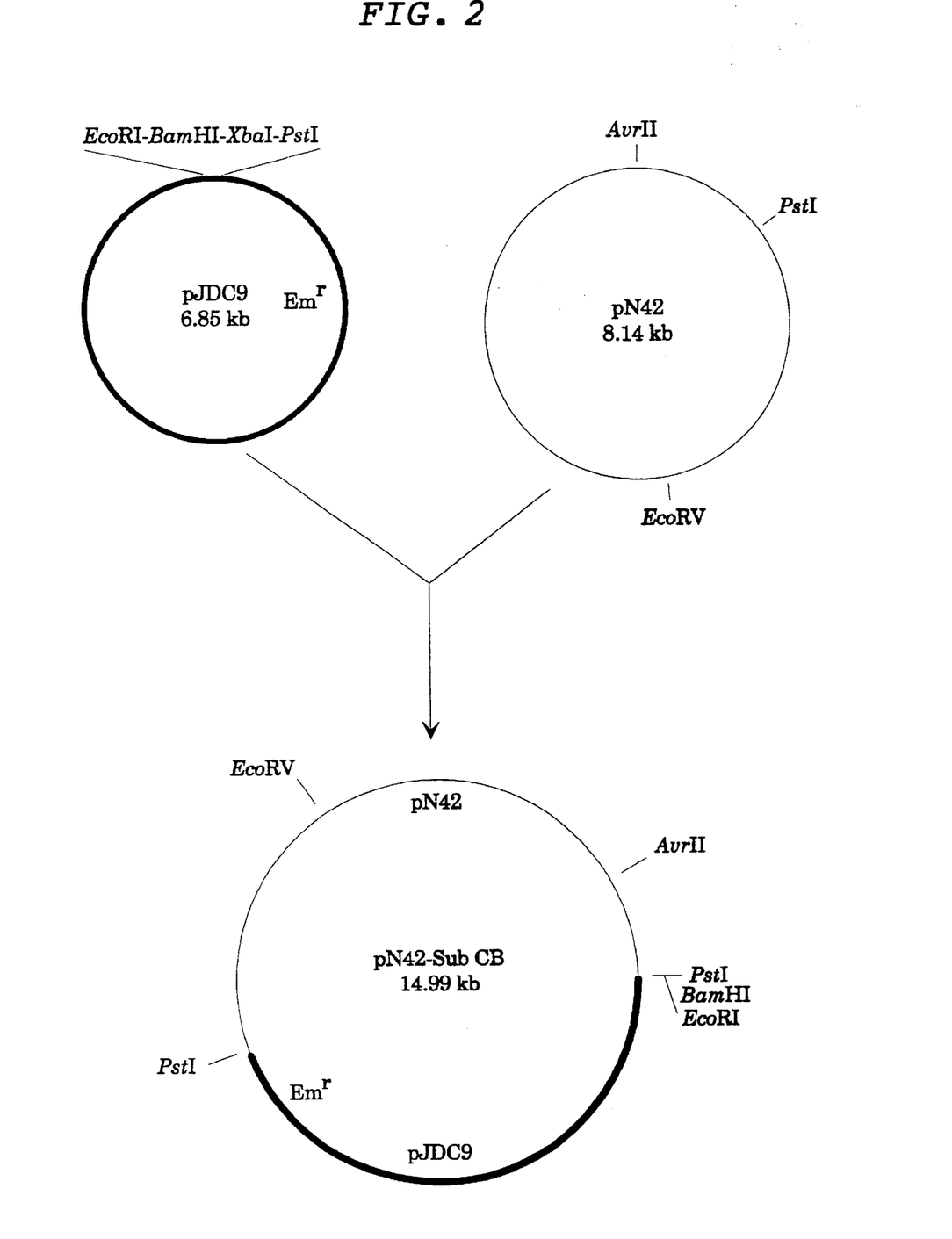
Figure 3:
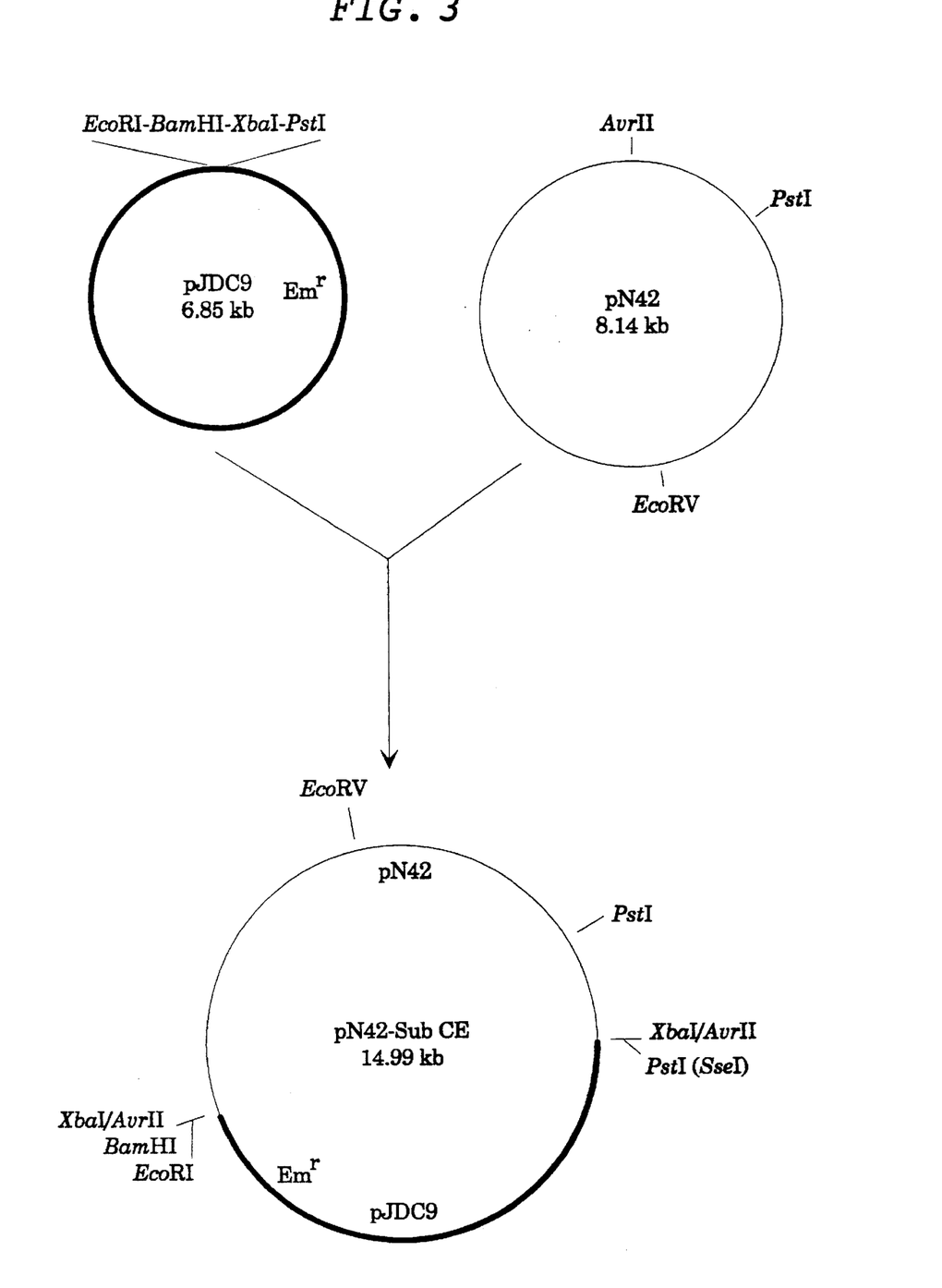

Analysis of over fifty L. delbrueckii sp. strains from the Nestlé culture collection identified one, N42, that contains an extra-chromosomal replication plasmid. This is designated pN42 (its restriction map is shown in the FIG. 1)and chosen for analysis as it must contain all of the plasmid encoded trans and cis elements necessary for its replication in L. bulgaricus. The integrity of N42 as a L. delbrueckii sp. is ascertained by API tests and molecular characterization of hybridization with the L. delbrueckii specific probe (Delley M., Mollet B., and Hottinger H., 1990, DNA probe for Lactobacillus delbrueckii, Appl. Environ. Microbiol, 56:1967–1970).

pN42 plasmid DNA is isolated by cesium chloride-ethidium bromide buoyant density gradients for restriction mapping and sub cloning. Plasmid pN42 is cloned in its entirety into the E. coli vector pJDC9 (J.-D. Chen and D. A. Morrisson 1987, Cloning of Streptococcus pneumoniae DNA Fragments in Escherichia coli Requires Vector Protected by Strong Transcriptional Terminators, Gene 55, 179–187) at several identified unique restriction sites PstI (pN42-Sub CB), AvrII (pN42-Sub CE) or into the pUC/pK plasmids for DNA sequence analysis.

pN42 plasmid DNA is digested with the restriction enzyme PstI, mixed with PstI digested and dephosphorylated pJDC9 vector, ligated and transformed into E. coli. Colonies are analyzed by restriction enzyme digestions and a positive clone designated pN42-Sub CB (FIG. 2).

pN42 plasmid DNA is digested with the restriction enzyme AvrII, mixed with XbaI digested and dephosphorylated pJDC9 vector, ligated and transformed into E. coli. Colonies are analyzed by restriction enzyme digestions and a positive clone designated pN42-Sub CE (FIG. 3).

Figure 4:
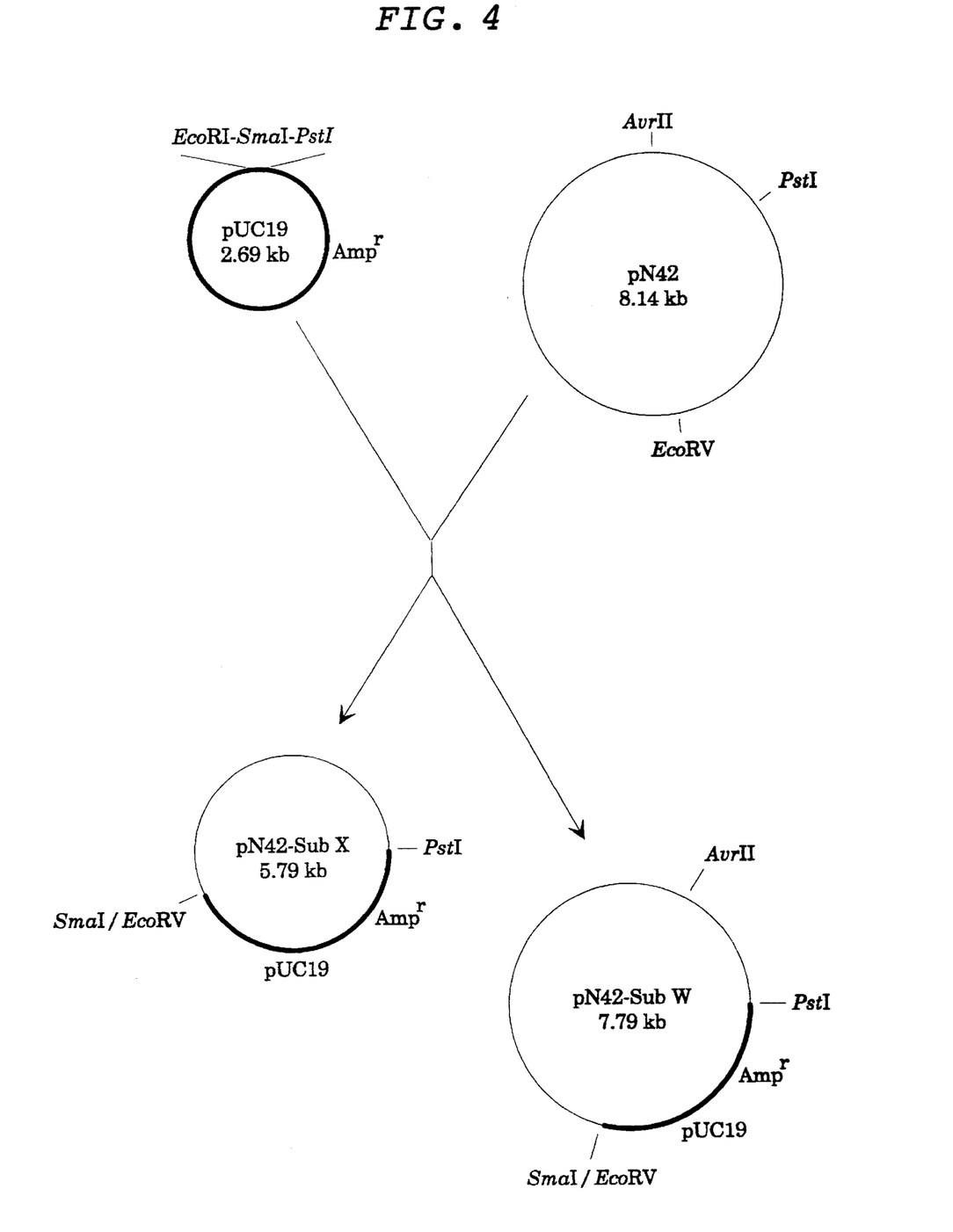

Plasmid pN42-Sub CB is digested with the restriction enzymes EcoRV and PstI, the DNA fragments separated on an agarose gel and the 3.1 kb and 5.1 kb fragments purified. These two fragments are mixed with PstI and SmaI digested and dephosphorylated pUC19 vector, ligated and transformed into E. coli. Colonies are analyzed by restriction enzyme digestions and the positive clones designated PN42-Sub W and pN42-Sub X (for the 5.1 kb and 3.1 kb fragments respectively) (FIG. 4).

The complete DNA sequence of pN42 is determined from subclones from synthetic oligonucleotide primers on both strands by the dideoxy chain termination reactions using the $^{77}$sequencing® kit of Pharmacia and $^{35}$SdATP. pN42 consists of a circular double stranded plasmid of 8140 base pairs with at least five open reading frames (designated ORF1 to ORF5) of 50 amino acids or more as identified by the computer program "Frames" from the GCG suite (Computer software is from Genetics Computer Group Inc. (GCG), Devereux J., Haeberli P. and Smithies O. (1984), A comprehensive set of sequence analysis programs for the VAX. Nucleic Acids Res. 12:387–395). The GCG program "Repeat" identified a three times twenty-one base pair direct repeat which is the potential origin of replication. The restriction map of pN42 is shown in FIG. 1 and the complete DNA sequence in sequence listing 1 (SEQ ID N° 1).

The DNA sequence analysis of pN42 allows the definition of structural features that may be important for the replication of the plasmid in L. delbrueckii sp. and the construction of shuttle vectors that include all these features intact (the introduction of genes may be obtained by cloning pN42 at the following restriction sites Avr II, NsiI, SphI, Nb plasmid DNA isolated from Lactobacillus delbueckii sp. digested at only one of the five SphI sites I.E. at bp 7882).

This ensures that the said shuttle vector must replicate when transformed into L. bulgaricus.

Figure 5:
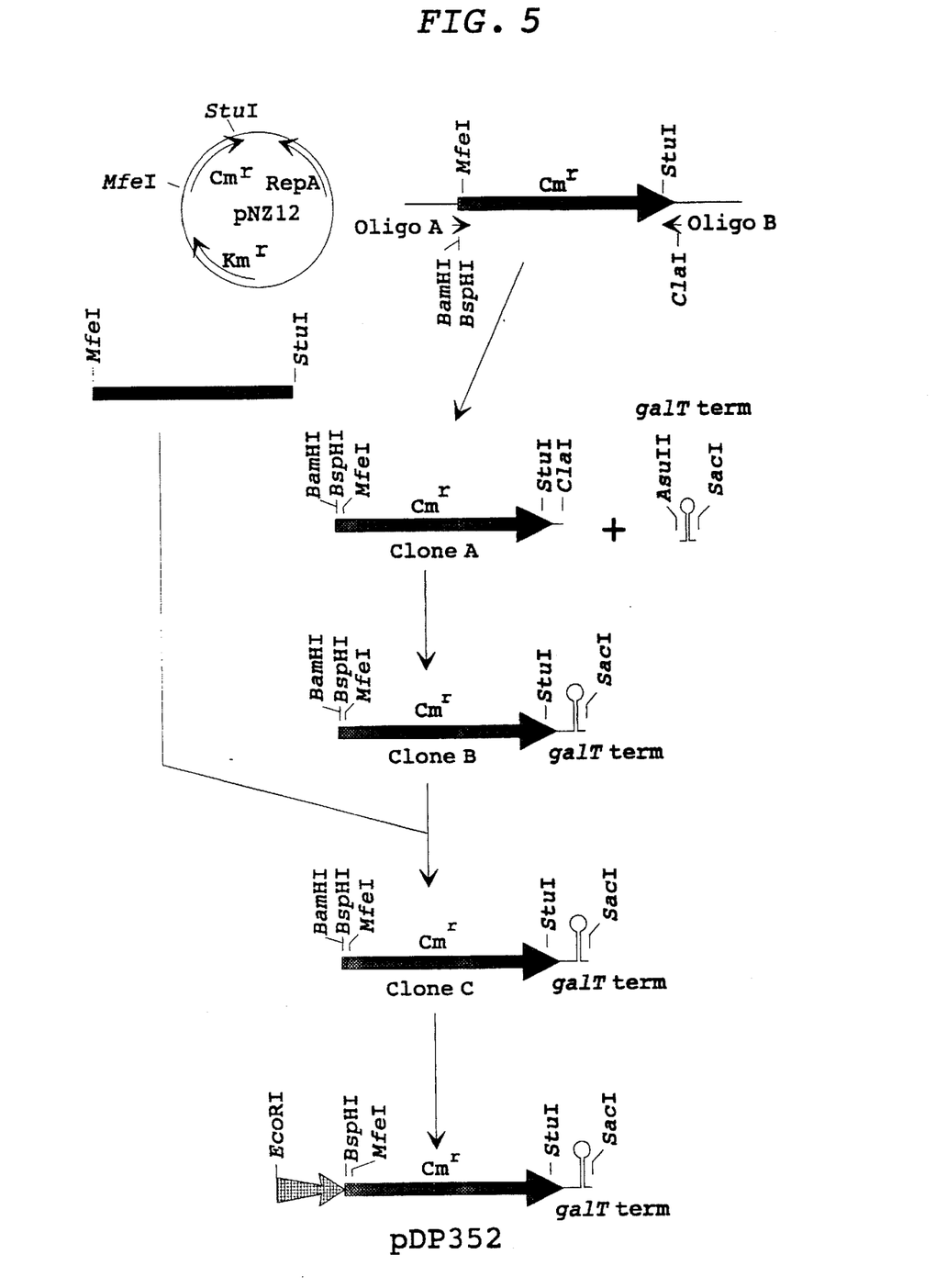

It is judged probable that antibiotic resistance conferred by a defined resistance gene may be transferred to any other organism if it contains the appropriate translation/transcriptional control signals. Therefore the defined gram positive chloramphenicol resistance gene (chloramphenicol acetyltransferase, CAT originally from Staphylococcus aureus) is been taken from the broad host range plasmid pNZ12 (W. M. de Vos, 1987, Gene Cloning and Expression in Lactic Streptococci, FEMS Microbiol. Reviews, 46, 281–295) and used to engineer the bona fide L. bulgaricus promoter from the lacS-Z operon (P. Leong-Morgenthaler, M. C. Zwahlen and H. Hottinger, 1991, Lactose Metabolism in Lactobacillus bulgaricus: Analysis of the Primary Structure and Expression of the Genes Involved, J. Bacteriol., 173, 1951–1957). This is followed with a gram positive stem-loop terminator from the lactose-galactose operon of Lc. lactis strain NCDO2054. The complete construction is shown in FIG. 5.

The plasmid pKN19 is the E. coli cloning vector pK 19 (R. D. Pridmore, 1987, New and Versatile Cloning Vectors with Kanamycin-Resistance, Gene, 56, 309–312) where the unique BspHI restriction site in a non essential region is destroyed by restriction enzyme digestion and the four base overhang repared with Klenow enzyme and the four nucleotides according to Maniatis et al. (T. Maniatis, E. F. Fritch and J. Sambrook, Molecular cloning a laboratory manual, Cold Spring Harbor Laboratory, Cold Spring Harbor, N.Y., 1982). The chloramphenicol resistance gene from pNZ12 is extracted by PCR amplification (Saiki R. K., Gelfand D. H., Stoffel S., Scharf S. J., Higuchi R., Horn G. T., Mullis K. B., and Ehrlich H. A., 1988, Primer-directed enzymatic amplification of DNA with a thermostable DNA polymerase. Science, 239:487–491; Saiki R. K., Scharf S., Faloona F., Mullis K. B., Horn G. T., Ehrlich H. A. and Arnheim N., 1985, Enzymatic amplification of β-globin genomic sequences and restriction site analysis for diagnosis of sickle cell anemia, Science 230:1350–1354) using the mutagenic primers A (5'-AGGAGGATCCTCTCATGAACTTTAATAAAATTG) (SEQ ID NO.3) that introduced a BspHI restriction site overlapping the ATG initiation codon of the CAT gene, plus primer B (5'-TACAGTATCGATTATCTCATATTATA) (SEQ ID NO. 4) that introduces a ClaI restriction site 9 bp down stream of the CAT gene. The PCR amplification is performed on 50 ng of BglII digested pNZ12 DNA with 0.3 µM each of oligonucleotides C plus D, 200 µM of the four nucleotides and PCR cycling at 94° C. for 0.5 minutes, 50° C. for 0.5 minutes, 72° C. for 0.5 minutes for a total of 30 cycles.

The product is digested with the restriction enzymes ClaI plus BamHI and the 660 bp fragment purified from an agarose gel and cloned into the E. coli vector pBS KS+® (Stratagene Corp.) also digested with ClaI, BamHI and dephosphorylated. The ligated fragments are transformed into E. coli and plated onto LB plates supplemented with ampicillin, 5-bromo-4-chloro-3-indolyl-(3-D-galactopyranoside) (X-Gal) and isopropyl-β-D-thiogalactopyranoside (IPTG). Clones are screened by restriction enzyme digestions, a positive clone chosen and designated clone A; both chloramphenicol and ampicillin resistant. Clone A is digested with restriction enzymes MfeI, StuI and dephosphorylated. This fragment is replaced by the equivalent CAT MfeI-StuI fragment from pNZ12. This is to eliminate any PCR induced mutations within the CAT gene, giving Clone B. (This step is not shown in FIG. 5).

Clone B is digested with the restriction enzymes BamHI plus ClaI and the 660 bp fragment purified from an agarose gel. pKN19/galT-term is pKN19 containing the Lc. lactis NCDO2054 lactose-galactose operon terminator as an SpeI-SacI restriction fragment, with its internal BspHI restriction site destroyed as described above. pKN19/galT-term is digested with the restriction enzymes SfuI plus SacI (both sites natural to the fragment) and the 190 bp fragment purified from an agarose gel. These two fragments are mixed together with the vector pKN19 digested with the restriction enzymes SacI, BamHI plus dephosphorylated, ligated together and transformed into E. coli. Clones are screened by restriction enzyme digestions, a positive clone chosen and designated clone C.

The published L. bulgaricus lacS promoter is used to design two mutagenic oligonucleotides, C (5'-ATTGGAAGAATTCACCAACGCTTTTCATTTC) (SEQ ID NO. 5) which introduces an EcoRI restriction site 240 bp upstream of the ATG initiation codon and oligonucleotide D (5'-GGTGGTGACGAAGACGATA) (SEQ ID NO. 6) which primes 110 bp down stream of the ATG of the lacS gene which naturally contains a BspHI restriction site overlapping the start codon. The PCR amplification is performed on 100 ng of genomic L. delbrueckii sp. DNA with 0.3 µM each of oligonucleotides C plus D, 200 µM of the four nucleotides and PCR cycling at 94° C. for 0.5 minutes, 50° C. for 0.5 minutes, 72° C. for 0.5 minutes and a total of 30 cycles. The PCR product is digested with the restriction enzymes EcoRI plus BspHI and the 250 bp fragment purified from an agarose gel. Clone D is digested with the restriction enzymes BspHI plus SacI and the 780 bp fragment purified from an agarose gel. These two fragments are ligated together into EcoRI, SacI plus dephosphorylated pKN19 vector, transformed into E. coli, and plated onto LB plates supplemented with kanamycin. Clones are screened by restriction enzyme digestions, a positive clone chosen and designated pDP352 the complete DNA sequence of which is given in sequence listing 2 (SEQ ID No. 2).

The chloramphenicol resistance gene constructed in pDP352 is transcribed from a bona fide L. bulgaricus promoter that is constitutively expressed in this host. This includes the natural promoter elements of −35, −10 regions and the ribosome binding site at exactly the same relative position to the ATG of the chloramphenicol resistance gene as to the original ATG of the lacS gene. This ensures that the chloramphenicol resistance gene will be correctly transcribed and translation initiated at the correct position and that the resistance gene will work.

Figure 6:
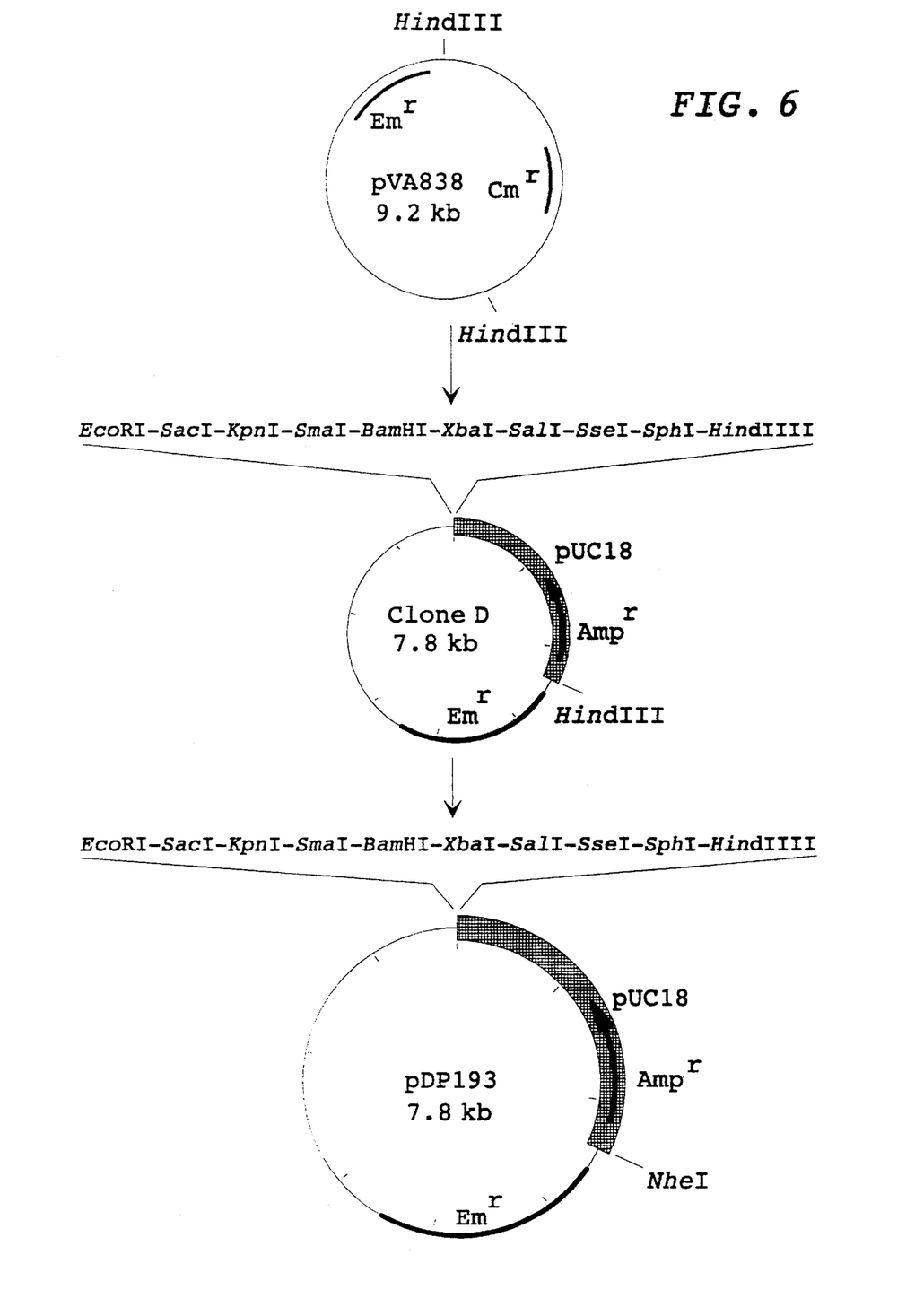

The E. coli-Lc. lactis shuttle vector pDP193 is constructed from the E. coli vector pUC18 (R. D. Pridmore, 1987, New and Versatile Cloning Vectors with Kanamycin-Resistance, Gene, 56, 309–312) plus the plasmid pVA749 (F. L. Macrina, J. A. Tobian, K. R. Jones and R. P. Evans, Molecular cloning in the Streptococci, in A. Hallaender, R. DeMoss, S. Kaplan, S. Konisky, D. Savage and R. Wolve (Eds.), Genetic engineering of microorganisms for chemicals, Plenum, New York, 1982, pp. 195–210). pVA749 is extracted from the chimeric plasmid pVA838 (F. L. Macrina, J. A. Tobian, K. R. Jones, R. P. Evans and D. B. Clewell, 1982, A Cloning Vector able to Replicate in Escherichia coli and Streptococcus sanguis, Gene, 19, 345–353) as a HindIII restriction fragment and cloned into the HindIII site of pUC18. The second HindIII site opposite to the pUC cloning array is removed by Klenow enzyme end repair. pVA749 itself consists of a gram positive plasmid origin of replication from Streptococcus faecalis (capable of replication in Lc. lactis) and the erythromycin resistance gene from pAMβ1. The construction of pDP193 is depicted in FIG. 6.

Plasmid pVA838 is digested with the restriction enzyme HindIII, the fragments separated on an agarose gel and the 5.2 kb pVA749 fragment purified. Vector pUC18 is digested with the restriction enzyme HindIII, dephosphorylated, mixed with the pVA749 fragment, ligated and transformed into E. coli. Colonies are analyzed by restriction enzyme digestions and a positive clone designated Clone D. Clone D is digested with the restriction enzyme HindIII in the presence of 50 µg/ml ethidium bromide (M. Osterlund, H. Luthman, S. V. Nilsson and G. Magnusson (1982), Ethidium-bromide-inhibited restriction endonucleases cleave one strand of circular DNA, Gene 20, 121–125), the fragments separated on an agarose gel and the linear 7.9 kb fragment purified. The four base overhang generated by HindIII in the linear Clone D is filled in with Klenow enzyme in the presence of four nucleotides according to Maniatis et al. (T. Maniatis, E. F. Fritch and J. Sambrook, Molecular cloning a laboratory manual, Cold Spring Harbor Laboratory, Cold Spring Harbor, N.Y., 1982), ligated and transformed into E. coli. Colonies are analyzed by restriction enzyme digestions and a positive clone designated pDP193.

Figure 7:
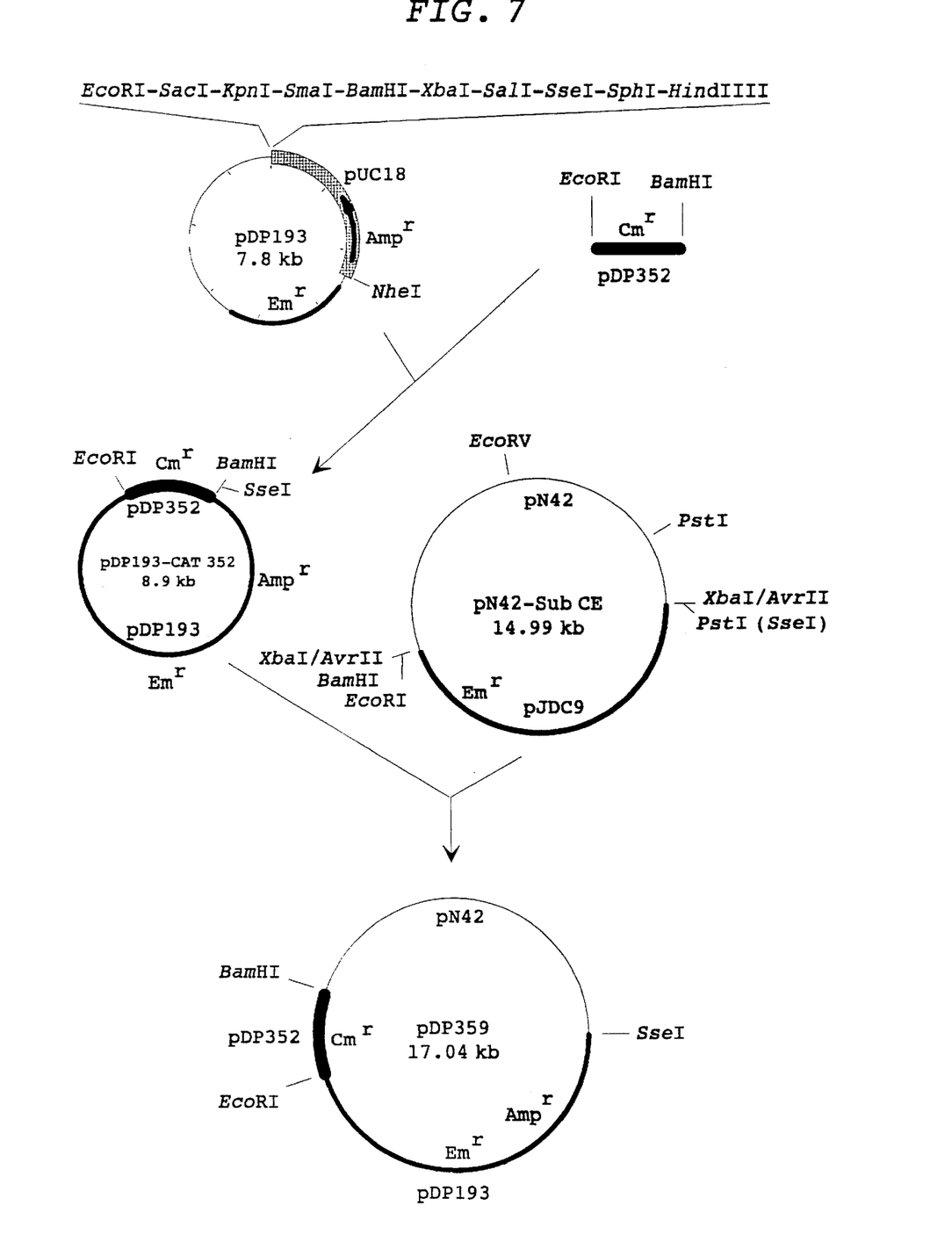

Plasmid pDP193 is digested with the restriction enzymes SacI plus EcoRI and dephosphorylated. pDP352 is digested with the restriction enzymes SacI plus EcoRI and the 1100 bp CAT gene purified from an agarose gel. These two are mixed together, ligated and electrotransformed into the Lc. lactis plasmid free strain LM0230. Positive colonies are identified as erythromycin plus chloramphenicol resistant and confirmed by restriction enzyme digestions. A positive clone is chosen and designated pDP193-CAT 352.

pDP193-CAT 352 is digested with the restriction enzymes SseI plus BamHI and dephosphorylated. Plasmid pN42-Sub CE is digested with the restriction enzymes SseI plus BamHI (both sites from the linker) and the 9.3 kb fragment purified from an agarose gel. These two fragments are mixed, ligated and electrotransformed into Lc. lactis strain LM0230. Clones are screened by restriction enzyme digestions, a positive clone chosen and designated pDP359 as shown in FIG. 7.

The vector pDP359 satisfies the requirements for a shuttle vector for L. bulgaricus that must work in this host. It includes a complete bona fide replicating plasmid isolated and characterized from L. delbrueckii sp. plus a chloramphenicol resistance gene that is transcribed from a native L. bulgaricus promoter. These considerations ensure that the said plasmid pDP359 which replicate when introduced into L. bulgaricus.

What is claimed is:

1. An isolated plasmid derived from *Lactobacillus delbrueckii* sp. having a sufficient amount of the restriction map of FIG. 1 so as to provide all of the plasmid encoded trans and cis elements necessary for replication of the plasmid in *Lactobacillus bulgaricus*.

2. An isolated plasmid according to claim 1, having the entire restriction map of FIG. 1.

3. An isolated plasmid according to claim 1, comprising the DNA sequence of SEQ ID NO:1.

4. A recombinant vector comprising:

a plasmid according to claim 1;

at least one DNA sequence capable of replication in *E. coli* and/or *Lc. lactis*; and at least one marker gene.

5. A vector according to claim 4, wherein said marker gene is a chloramphenicol resistance gene.

6. A vector according to claim 4, wherein said marker gene is transcribed from a native *L. bulgaricus* promoter.

7. A vector according to claim 4, wherein said marker gene is followed with a gram positive stem-loop terminator.

8. A microorganism transformed by a plasmid according to claim 1 or a vector according to claim 4.

9. A microorganism according to claim 8, wherein said microorganism is *Lactobacillus bulgaricus*.

10. A method of transforming a microorganism, comprising introducing into said microorganism a plasmid according to claim 1 or a vector according to claim 4.

* * * * *